United States Patent
Li et al.

(10) Patent No.: US 11,170,506 B2
(45) Date of Patent: Nov. 9, 2021

(54) METHOD FOR CONSTRUCTING SEQUENCING TEMPLATE BASED ON IMAGE, AND BASE RECOGNITION METHOD AND DEVICE

(71) Applicant: GENEMIND BIOSCIENCES COMPANY LIMITED, Shenzhen (CN)

(72) Inventors: Linsen Li, Shenzhen (CN); Weibin Xu, Shenzhen (CN); Huan Jin, Shenzhen (CN); Zefei Jiang, Shenzhen (CN); Zhiliang Zhou, Shenzhen (CN); Qin Yan, Shenzhen (CN)

(73) Assignee: GENEMIND BIOSCIENCES COMPANY LIMITED, Shenzhen (CN)

( * ) Notice: Subject to any disclaimer, the term of this patent is extended or adjusted under 35 U.S.C. 154(b) by 0 days.

(21) Appl. No.: 17/270,418

(22) PCT Filed: Aug. 22, 2018

(86) PCT No.: PCT/CN2018/101819
§ 371 (c)(1),
(2) Date: Feb. 22, 2021

(87) PCT Pub. No.: WO2020/037574
PCT Pub. Date: Feb. 27, 2020

(65) Prior Publication Data
US 2021/0217171 A1  Jul. 15, 2021

(51) Int. Cl.
*G06T 7/00* (2017.01)
*G06T 7/33* (2017.01)
(Continued)

(52) U.S. Cl.
CPC ............ *G06T 7/0014* (2013.01); *G06T 5/002* (2013.01); *G06T 5/003* (2013.01); *G06T 5/50* (2013.01); *G06T 7/337* (2017.01); *G16B 30/00* (2019.02)

(58) Field of Classification Search
CPC .. C12Q 1/6869; G06K 9/0014; G06K 9/6255; G06K 2209/07; G06T 5/002;
(Continued)

(56) References Cited

U.S. PATENT DOCUMENTS 7,732,138 B2 * 6/2010 Tam .................. G01N 33/5308
435/6.11
8,965,076 B2 * 2/2015 Garcia .................... G06T 7/246
382/128

(Continued)

FOREIGN PATENT DOCUMENTS

CN   101206116 A    6/2008
CN   101930116 A   12/2010
(Continued)

OTHER PUBLICATIONS

Ye Binggang, High-throughput Genome Sequencing Image Processing and Data Analysis, China doctoral dissertation full text database, vol. 11, p. 34-35, 46-49, Nov. 15, 2010.
(Continued)

*Primary Examiner* — Mekonen T Bekele
(74) *Attorney, Agent, or Firm* — Dilworth IP, LLC

(57) ABSTRACT

A method for constructing a sequencing template based on an image, a device, and a system. The image includes first, second, third and fourth images of one same field of view corresponding to base extensions of A, T/U, G, and C respectively; the first, second, third and fourth images respectively include images M1 and M2, images N1 and N2, images P1 and P2, and images Q1 and Q2; the method
(Continued)

includes combining any two of the images M1, M2, N1, N2, P1, P2, Q1, and Q2 to perform bright spot matching, and enabling such images to participate in the combination for at least one time to obtain a plurality of combined images including first coincident bright spots, and merging the first coincident bright spots on the plurality of combined images to obtain a bright spot set corresponding to the sequencing template.

20 Claims, 3 Drawing Sheets

(51) Int. Cl.
*G16B 30/00* (2019.01)
*G06T 5/00* (2006.01)
*G06T 5/50* (2006.01)

(58) Field of Classification Search
CPC .. G06T 5/003; G06T 5/50; G06T 7/00; G06T 7/0014; G06T 7/337; G16B 30/00
See application file for complete search history.

(56) References Cited

U.S. PATENT DOCUMENTS

| | | | | |
|---|---|---|---|---|
| 2009/0129647 | A1* | 5/2009 | Dimitrova | G16B 45/00 382/129 |
| 2009/0319591 | A1* | 12/2009 | Allen | C12Q 1/6813 708/250 |
| 2012/0020537 | A1* | 1/2012 | Garcia | G06T 7/33 382/129 |
| 2014/0349281 | A1 | 11/2014 | Jennings | |
| 2015/0317433 | A1 | 11/2015 | Kermani et al. | |
| 2019/0323079 | A1* | 10/2019 | Drmanac | C12Q 1/6869 |
| 2020/0302225 | A1* | 9/2020 | Dutta | G06K 9/036 |

FOREIGN PATENT DOCUMENTS

| | | | |
|---|---|---|---|
| CN | 101950419 A | | 1/2011 |
| CN | 102174384 A | | 9/2011 |
| CN | 102354398 A | | 2/2012 |
| CN | 102663720 A | | 9/2012 |
| CN | 103582697 A | | 2/2014 |
| CN | 104297249 A | | 1/2015 |
| CN | 104318568 A | | 1/2015 |
| CN | 104376537 A | | 2/2015 |
| CN | 105039147 A | | 11/2015 |
| CN | 105205788 A | | 12/2015 |
| CN | 105303533 A | | 2/2016 |
| CN | 105389581 A | | 3/2016 |
| CN | 105524827 A | | 4/2016 |
| CN | 105524827 A | * | 4/2016 |
| CN | 105551034 A | | 5/2016 |
| CN | 105741266 A | | 7/2016 |
| CN | 106295124 A | | 1/2017 |
| CN | 107918931 A | | 4/2018 |
| CN | 107945150 A | | 4/2018 |
| CN | 108229098 A | | 6/2018 |
| JP | 2007315772 A | | 12/2007 |
| KR | 101348680 B1 | | 1/2014 |
| WO | 2016107896 A1 | | 7/2016 |

OTHER PUBLICATIONS

Julien Ghaye et al, Image Thresholding Techniques for Localization of Sub-Resolution Fluorescent Biomarkers, International Society for Advancement of Cytometry (ISAC), Cytometry Part A, 83A, p. 1001-1016, 2013.
Feng He et al, A Laplacian of Gaussian-Based Approach for Spot Detection in Two-Dimensional Gel Electrophoresis Images, 4th Conference on Computer and Computing Technologies in Agriculture (CCTA), Nanchang, China, 10.1007/978-3-642-18369-0_2. hal-01564853, 9 pages, Oct. 2010.
Ihor Smal, Quantitative Comparison of Spot Detection Methods in Fluorescence Microscopy, IEEE Transactions on Medical Imaging, vol. 29, No. 2, p. 282-301, Feb. 2010.
Kenji Takita et al, High-Accuracy Subpixel Image Registration Based on Phase-Only Correlation, IEICE Trans. Fundamentals, vol. E86-A, No. 8, Aug. 2003.
International Search Report for PCT/CN2019/101819; dated May 21, 2019, 6 pages.
Written Opinion of the International Searching Authority for PCT/CN2018/101819; dated May 21, 2019, 8 pages.
European Patent Office Communication pursuant to Rule 164(1) EPC for App. No. EP18930701.0, dated Jul. 15, 2021, 18 pages.
Abhishek Mitra et al.: "Strategies for Achieving High Sequencing Accuracy for Low Diversity Samples and Avoiding Sample Bleeding Using Illumina Platform", PLOS ONE, vol. 10, No. 4, Jan. 1, 2015 (Jan. 1, 2015), pp. 1-21, XP055669098, DOI: 10.1371/journal.pone.0120520.
John F. Thompson et al: "Single Molecule Sequencing with a HeliScope Genetic Analysis System" In: "Current Protocols in Molecular Biology", Oct. 1, 2010 (Oct. 1, 2010), John Wiley & Sons, Inc., Hoboken, NJ, USA, XP055086250, ISBN: 978-0-47-114272-0 pp. 7.10.1-7.10.14, DOI: 10.1002/0471142727.mb0710592.
Christian Korfhage et al., "Clonal rolling circle amplification for on-chip DNA cluster generation", Biology Methods and Protocols, vol. 2, No. 1, Jan. 1, 2017, XP055675828.

* cited by examiner

METHOD FOR CONSTRUCTING SEQUENCING TEMPLATE BASED ON IMAGE, AND BASE RECOGNITION METHOD AND DEVICE

TECHNICAL FIELD

The present disclosure relates to the fields of image processing and information identification, and in particular to a method for constructing a sequencing template based on images, a method for base calling, a device for constructing a sequencing template based on images, a device for base calling, and a computer program product.

BACKGROUND

In the related art, including in a sequencing platform acquiring multiple images of a nucleic acid molecule (template) in biochemical reaction based on an imaging system to determine the nucleotide sequence of the nucleic acid molecule, how to process and correlate multiple images (including information in the images) acquired at different time points to effectively and accurately acquire at least part of the nucleotide composition and sequence of a template nucleic acid is a matter of concern.

SUMMARY

The embodiments of the present disclosure are intended to solve at least one of the technical problems existing in the prior art or at least provide an alternative practical solution.

According to one embodiment of the present disclosure, a method for constructing a sequencing template based on images is provided. The images comprise a first image, a second image, a third image and a fourth image of the same field of view respectively corresponding to base extensions of four types of bases A, T/U, G and C. A plurality of nucleic acid molecules with an optically detectable label are present in this field of view during the base extension, and at least part of the nucleic acid molecules are present as spots in the images. Sequential and/or simultaneous completion of the base extensions of the four types of bases once is defined as one cycle of sequencing. The first image comprises an image M1 and an image M2, the second image comprises an image N1 and an image N2, the third image comprises an image P1 and an image P2, and the fourth image comprises an image Q1 and an image Q2. The images M1 and M2 respectively come from two cycles of sequencing, the images N1 and N2 respectively come from two cycles of sequencing, the images P1 and P2 respectively come from two cycles of sequencing, and the images Q1 and Q2 respectively come from two cycles of sequencing. The method comprises: combining any two of the images M1, M2, N1, N2, P1, P2, Q1 and Q2 for spot matching, such that the images M1, M2, N1, N2, P1, P2, Q1 and Q2 each participate in at least one combination to give a plurality of combination images each comprising a first overlap spot, with two or more spots distanced by less than a first predetermined pixel on a combination image being defined as a first overlap spot; and merging the first overlap spots on the plurality of combination images to give a spot set corresponding to the sequencing template.

According to one embodiment of the present disclosure, a device for constructing a sequencing template based on images is provided, which is used to implement all or part of the steps of the method for constructing a sequencing template based on images according to the aforementioned embodiment of the present disclosure. The images comprise a first image, a second image, a third image and a fourth image of the same field of view respectively corresponding to base extensions of four types of bases A, T/U, G and C. A plurality of nucleic acid molecules with an optically detectable label are present in this field of view during the base extension, and at least part of the nucleic acid molecules are present as spots in the images. Sequential and/or simultaneous completion of the base extensions of the four types of bases once is defined as one cycle of sequencing. The first image comprises an image M1 and an image M2, the second image comprises an image N1 and an image N2, the third image comprises an image P1 and an image P2, and the fourth image comprises an image Q1 and an image Q2. The images M1 and M2 respectively come from two cycles of sequencing, the images N1 and N2 respectively come from two cycles of sequencing, the images P1 and P2 respectively come from two cycles of sequencing, and the images Q1 and Q2 respectively come from two cycles of sequencing. The device comprises: a combining unit, configured for combining any two of the images M1, M2, N1, N2, P1, P2, Q1 and Q2 for spot matching, such that the images M1, M2, N1, N2, P1, P2, Q1 and Q2 each participate in at least one combination to give a plurality of combination images each comprising a first overlap spot, with two or more spots distanced by less than a first predetermined pixel on a combination image being defined as a first overlap spot; and a merging unit, configured for merging the first overlap spots on the plurality of combination images to give a spot set corresponding to the sequencing template.

According to one embodiment of the present disclosure, a computer-readable storage medium for storing a program executed by a computer is provided, wherein executing the program comprises implementing the method for constructing a sequencing template based on images according to any of the aforementioned embodiments. The computer-readable storage medium includes, but is not limited to, read-only memories, random access memories, magnetic disks, optical disks, or the like.

According to one embodiment of the present disclosure, a terminal, a computer program product, is also provided. The product comprises an instruction that causes a computer to execute the method for constructing a sequencing template based on images according to the aforementioned embodiment of the present disclosure when the program is executed by the computer.

The sequencing template constructed by the method and device for constructing a sequencing template based on images, the computer-readable storage medium and/or the computer program product above is a spot set corresponding to the sequencing template, and the spot set can effectively, accurately and comprehensively reflect the information of the sequencing template, which is favorable for further accurate base calling, i.e. the accurate identification and acquisition of nucleotide sequences of at least part of a template nucleic acid.

According to another embodiment of the present disclosure, a method for base calling is provided, comprising: matching spots on images acquired from a base extension to a spot set corresponding to a sequencing template, and performing base calling according to the matched spots, wherein a plurality of nucleic acid molecules with an optically detectable label are present in the field of view corresponding to the images acquired from the base extension, at least part of the nucleic acid molecules are present as spots in the images acquired from the base extension, and the spot set corresponding to the sequencing template is constructed by the method and device for constructing a sequencing template based on images, the computer-readable storage medium and/or the computer program product according to aforementioned embodiments of the present disclosure.

According to one embodiment of the present disclosure, a device for base calling configured for implementing the method for base calling according to an aforementioned embodiment of the present disclosure is provided. The device is configured for: matching spots on images acquired from a base extension of a base to a spot set corresponding to a sequencing template, and performing base calling according to the matched spots, wherein a plurality of nucleic acid molecules with an optically detectable label are present in the field of view corresponding to the images acquired from the base extension, at least part of the nucleic acid molecules are present as spots in the images acquired from the base extension, and the spot set corresponding to the sequencing template is constructed by the method and/or device for constructing a sequencing template based on images according to the aforementioned embodiments of the present disclosure.

According to one embodiment of the present disclosure, a computer-readable storage medium for storing a program executed by a computer is provided, wherein executing the program comprises implementing the method for base calling according to any of the aforementioned embodiments. The computer-readable storage medium includes, but is not limited to, read-only memories, random access memories, magnetic disks, optical disks, or the like.

According to one embodiment of the present disclosure, a computer program product comprising an instruction for base calling is also provided, wherein the instruction causes a computer to execute the method for base calling according to the aforementioned embodiment of the present disclosure when the program is executed by the computer.

Based on a constructed spot set corresponding to a sequencing template, the method and device for base calling, the computer-readable storage medium and/or the computer program product can be utilized to identify the bases bound with template nucleic acids during base extensions, and can be used for accurate sequencing of a template nucleic acid.

The additional aspects and advantages of the embodiments of the present disclosure will be partially set forth in the following description, and will partially become apparent from the following description or be appreciated by practice of the embodiments of the present disclosure.

DETAILED DESCRIPTION

Figure 1:
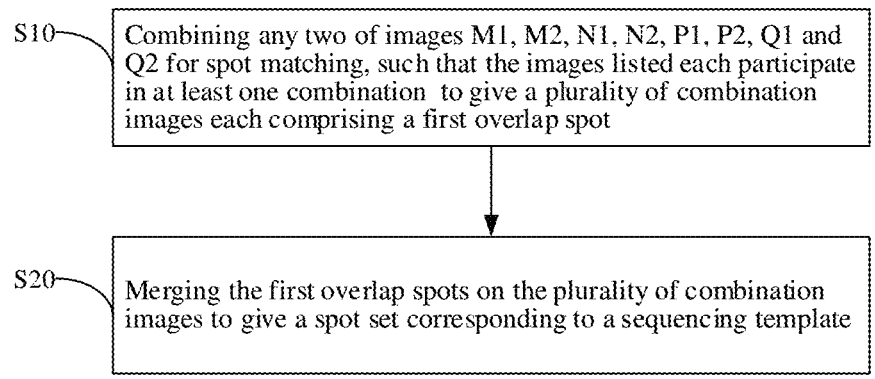
FIG. 1 is a schematic flowchart of a method for constructing a sequencing template based on images according to a specific embodiment of the present disclosure.

The embodiments of the present disclosure are described in detail below, and the examples of the embodiments are shown in the accompanying drawings, throughout which identical or similar reference numerals represent identical or similar elements or elements having identical or similar functions. The embodiments described below by reference to the accompanying drawings are exemplary and are merely intended to illustrate the present disclosure, but should not be construed as limiting the present disclosure. In the description of the present disclosure, the terms "first", "second", "third" and "fourth" are used for description purpose only rather than construed as indicating or implying relative importance or implicitly indicating the number or sequence of indicated technical features. In the description of the present disclosure, unless otherwise specifically defined, "a plurality of" means two or more than two.

Referring to FIG. 1, one embodiment of the present disclosure provides a method for constructing a sequencing template based on images. The images are acquired from the same field of view, comprising a first image, a second image, a third image and a fourth image of the same field of view respectively corresponding to base extensions of four types of bases A, T/U, G and C. A plurality of nucleic acid molecules with an optically detectable label are present in this field of view during the base extension, and at least part of the nucleic acid molecules are present as spots in the images. Sequential and/or simultaneous completion of the base extensions of the four types of bases one time is defined as one cycle of sequencing. The first image comprises an image M1 and an image M2, the second image comprises an image N1 and an image N2, the third image comprises an image P1 and an image P2, and the fourth image comprises an image Q1 and an image Q2. The images M1 and M2 respectively come from two sequencing, the images N1 and N2 respectively come from two sequencing, the images P1 and P2 respectively come from two sequencing, and the images Q1 and Q2 respectively come from two sequencing. The method comprises: S10, combining any two of the images M1, M2, N1, N2, P1, P2, Q1 and Q2 for spot matching, such that the images M1, M2, N1, N2, P1, P2, Q1 and Q2 each participate in at least one combination to give a plurality of combination images each comprising a first overlap spot, with two or more spots distanced by less than a first predetermined pixel on a combination image being defined as a first overlap spot; and S20, merging the first overlap spots on the plurality of combination images to give a spot set corresponding to the sequencing template. The "spot" or "peak" is a bright spot on an image, and a bright spot occupies at least one pixel. The "pixel point" is the same as "pixel".

The method can acquire a spot set corresponding to a template nucleic acid molecule by acquiring an intersection and then union of spots on a plurality of images. The sequencing template constructed by the method is a spot set corresponding to the sequencing template, and the spot set can effectively, accurately and comprehensively reflect the information of the sequencing template. The obtained spot set is favorable for further accurate base calling, i.e. for accurately acquiring the nucleotide sequence of at least part of a template nucleic acid molecules.

The one cycle of sequencing refers to sequential and/or simultaneous base extensions of four types of bases, may be a cycle of sequencing characterized by simultaneous base extensions of substrates (such as nucleotide analogues/base analogues) corresponding to four types of bases in one base extension system, a sequencing reaction characterized by completion of base extensions of two base analogues in one base extension system and base extensions of the other two substrates in another base extension system, or a sequencing reaction characterized by four base analogs being respectively added in four sequential base extension systems. It can be known that the first image, the second image, the third image and the fourth image may be acquired from two or more base extensions. In addition, a base extension may involve one or more image acquisitions.

In one example, the sequencing (reaction) comprises multiple base extension (reactions), such as one-color sequencing in which the substrates (nucleotide analogues) corresponding to the four types of bases contain the same fluorescent dye. One cycle of sequencing comprises four base extensions (4 repeats). For a field of view, one base extension involves one image acquisition, with the images M1, N1, P1 and Q1 being respectively acquired from the same field of view of the base extensions of the four types of bases in one cycle of sequencing.

In another example, for example in a single-molecule two-color sequencing reaction, two of the substrates (nucleotide analogues) corresponding to four types of bases used contain one fluorescent dye and the other two substrates contain another fluorescent dye with a different excitation wavelength. One cycle of sequencing comprises two base extensions, and the two base substrates with different dyes are subjected to a binding reaction in a base extension. For a field of view, one base extension involves two image acquisitions at different excitation wavelengths, with the images M1, N1, P1 and Q1 respectively acquired from the same field of view at two excitation wavelengths in two base extensions of a sequencing.

In yet another example, one cycle of sequencing comprises one base extension, such as a two-color sequencing reaction on a second generation sequencing platform, in which substrates (such as nucleotide analogues) corresponding to four types of bases contain dye a, dye b, dye a and dye b, and no dye, respectively, with the dye a and the dye b having different excitation wavelengths. The four substrates enable one cycle of sequencing in the same base extension. One base extension involves two image acquisitions at different excitation wavelengths, with the first image and the third image, the second image and the fourth image, and the image M1 and the image N1 respectively acquired from the same field of view of different sequencing or the same field of view at different excitation wavelengths of the same sequencing reaction.

In some specific embodiments, S20, merging the first overlap spots on the plurality of combination images comprises: performing one or more matchings between the first overlap spots on different combination images to give the spot set corresponding to the sequencing template. Thus, a set of accurate spots in one-to-one correspondence to the template nucleic acid molecule can be acquired, which is favorable for constructing an accurate template based on images.

In some embodiments, the images M1, N1, P1 and Q1 are sequentially acquired, and the images M2, N2, P2 and Q2 are sequentially acquired. That is, the images M1, N1, P1 and Q1 are acquired in one cycle of sequencing, and the images M2, N2, P2 and Q2 are acquired in another sequencing reaction. S10 comprises: combining the images M1, M2, N1, N2, P1, P2, Q1 and Q2 in pairs at an interval of S images to give K combination images, and discarding non-overlap spots on the combination images by matching spots on the combination images, wherein S is an integer from 0 to $S_{max}$, and $S_{max}$=total number of images participating in combination—4. It can be calculated that K=((the total number of images participating in combination B−S−1)+1)×(the total number of images participating in combination B−S−1)/2, i.e., $K=C_{(B-)}^2$. For example, when S=2, K=15. As such, a complete sequencing template can be constructed by using as little image information as possible.

For one cycle of sequencing comprising four base extensions, i.e. each base extension contains only one nucleotide analogue, preferably, S is greater than 1, and more preferably, S is greater than 2. This may help to prevent or reduce the interference of noise caused by factors of a biochemical experiment on the construction of a sequencing template based on images, and thereby a template can be determined effectively and accurately.

In one embodiment, the total number of images participating in combination is 12, and S=2. Thus, a complete sequencing temperature can be acquired, and the loss of reads can be reduced.

Figure 2:
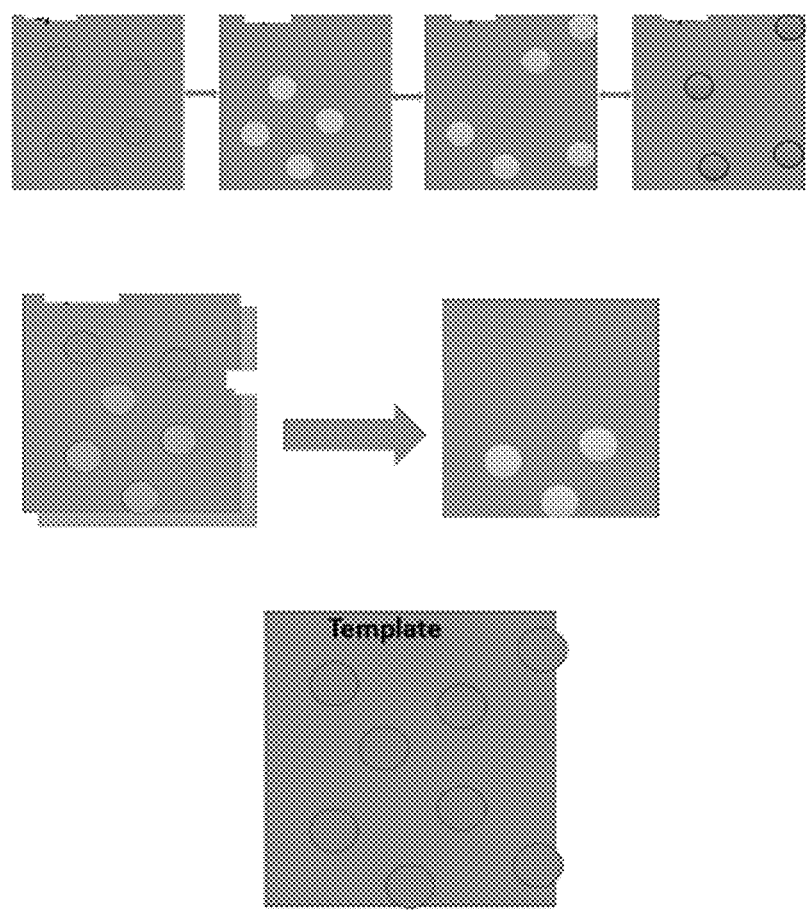
FIG. 2 is a schematic of combining and merging images Repeat1, Repeat5, Repeat6 and Repeat7 based on spots to construct a sequencing template according to a specific embodiment of the present disclosure.

In another embodiment, the total number of images participating in combination is 8, and S=2. When Repeat=5, the image Repeat1-5 (the image of Repeat1 and Repeat5) and the image Repeat2-5 are respectively subjected to overlap spot matching, and matching results are merged into a template container (Template; initially empty). In one example, as the image Repeat4 is used for the construction of a reference image, in order to reduce the calculation, template construction starts from the image Repeat5. When Repeat=6, the images Repeat1-6, Repeat2-6 and Repeat3-6 are respectively subjected to overlap spot matching, and matching results are then merged into Template. When Repeat=7, the images Repeat1-7, Repeat2-7, Repeat3-7 and Repeat4-7 are respectively subjected to overlap spot matching, and matching results are then merged into Template. When Repeat=8, the images Repeat1-8, Repeat2-8, Repeat3-8, Repeat4-8 and Repeat5-8 are respectively subjected to overlap spot matching, and matching results are then merged into Template. Finally, the spots in all the Template containers are counted and outputted, with the coordinates of each spot representing a chain, i.e., a read. After the template is constructed, the total number Total-Read of the reads can be known. FIG. 2 is a schematic of this process. The four images in FIG. 2 are Repeat1, Repeat5, Repeat6 and Repeat7 in sequence. The image change in the middle shows the process and result of overlap spot matching of the images Repeat1 and Repeat5. The lower panel shows the result of overlap spot matching of the images Repeat1, Repeat5, Repeat6 and Repeat7.

In one example, in an imaging system, the size of an electronic sensor is 6.5 μm, the magnification of a microscope is 60×, and the smallest size that can be seen is 0.1 μm. The size of a spot corresponding to a nucleic acid molecule is generally less than 10×10 pixels.

In one example, the first predetermined pixel is 1.05 pixel.

In one example, two first overlap spots distanced by greater than 1.85 pixel are set as two first overlap spots.

In one example, overlap spots which are greater than 1.05 pixel away from one overlap spot but less than 1.85 pixel away from another are discarded. As such, an accurate sequencing template can be constructed. In some specific embodiments, the images are registered images As such, a spot set corresponding to a sequencing template can be acquired accurately.

The embodiments of the present disclosure do not limit the method for image registration (i.e., correction). In some examples, the following method is employed to perform image registration, comprising: performing a first registration for an image to be registered based on a reference image, wherein the reference image and the image to be registered correspond to the same object and each comprise a plurality of spots, comprising: determining a first offset between a predetermined region on the image to be registered and a corresponding predetermined region in the reference image, and moving all spots on the image to be registered based on the first offset to give an image to be registered having undergone the first registration; and performing a second registration for the image to be registered having undergone the first registration based on the reference image, comprising: merging the image to be registered having undergone the first registration with the reference image to give a merging image, calculating an offset of all overlap spots in a predetermined region on the merging image to determine a second offset, two or more spots distanced by less than a predetermined pixel being defined as an overlap spot, and moving all spots on the image to be registered having undergone the first registration based on the second offset to register the image to be registered. The method for image registration through two associated registrations, which can be relatively referred to as coarse registration and fine registration including fine registration using spots on an image, can quickly complete high-precision image correction based on a small quantity of data, and is particularly suitable for scenarios where high-precision image correction is required, e.g., detection of images at the single molecule level, such as images acquired from a sequencing reaction on a third generation sequencing platform. The single molecule level means that resolution is the size of a single molecule or a few molecules, such as less than 10, 8, 5, 4 or 3 molecules.

In some specific embodiments, the image to be registered, i.e., an image for constructing the sequencing template, is acquired from a sequencing platform which performs sequencing based on the principle of optical imaging. Sequencing (also referred to as sequence determination) refers to nucleic acid sequencing, including DNA sequencing and/or RNA sequencing, and including long fragment sequencing and/or short fragment sequencing. The biochemical reactions for sequencing include base extensions. Sequencing can be performed through a sequencing platform, which may be selected from, but is not limited to, the Hisq/Miseq/Nextseq sequencing platform (Illumina), the Ion Torrent platform (Thermo Fisher/Life Technologies), the BGISEQ platform (BGI) and single-molecule sequencing platforms. The sequencing method may be selected from single-read sequencing and paired-end sequencing. The obtained sequencing results/data (i.e., read fragments) are referred to as reads, the length of which is referred to as read length. The "spot" corresponds to the optical signal of an extended base or base cluster.

The predetermined region on an image may be all or part of the image. In one example, the predetermined region on an image is part of the image, e.g., a 512×512 region at a center of the image. The center of the image is the center of the field of view. The point of intersection between the optical axis of the imaging system and the imaging plane may be referred to as a central point of the image, and a region centered on the central point may be regarded as a central area of the image.

In some specific embodiments, the image to be registered is acquired from a nucleic acid sequencing platform, which comprises an imaging system and a nucleic acid sample carrier system. The target nucleic acid molecules with optically detectable label are immobilized in a reactor, which is also referred to as a flowcell. The flowcell is fixed on a movable carrier, and is driven by the movable carrier to acquire images of the target nucleic acid molecules at different positions (different fields of view) in the flowcell. In general, precision limitations exist in the movement of the optical system and/or the movable carrier. For example, there may be a deviation between an arrival position specified by an instruction and a position at which the mechanical structure actually arrives, particularly in application scenarios requiring high precision. Therefore, in the process of moving hardware according to an instruction to perform multiple image acquisitions on the same position (field of view) at different time points, it is difficult to completely align the images of the same field of view acquired at the different time points. Correcting and aligning these images can help to accurately determine the nucleotide sequence of a nucleic acid molecule according to the change of information in the images acquired at multiple time points.

In some specific embodiments, the reference image is acquired by construction, and can be constructed when registration is performed for the image to be registered, or can be called when needed after being constructed and stored in advance.

In some examples, constructing a reference image comprises: acquiring a fifth image and a sixth image corresponding to the same object as the image to be registered; performing a coarse registration for the sixth image based on the fifth image, comprising: determining an offset between the sixth image and the fifth image, and moving the sixth image based on the offset to give a sixth image having undergone the coarse registration; and merging the fifth image with the sixth image having undergone the coarse registration to give the reference image, wherein the fifth image and the sixth image each comprise a plurality of spots. As such, an image containing more or relatively more complete information is acquired by construction and used as a basis for correction, which can facilitate more accurate image registration. For images acquired by nucleic acid sequence determination, constructing a reference image using multiple images helps to provide complete spot information corresponding to the nucleic acid molecule using the reference image, and is favorable for image correction based on spots.

In some embodiments, the fifth image and the sixth image are acquired at different times from the same field of view of a nucleic acid sequence determination reaction (sequencing reaction). In one example, a cycle of sequencing comprises a plurality of base extensions, such as one-color sequencing in which substrates (nucleotide analogues) corresponding to four types of bases used contain the same fluorescent dye, and one cycle of sequencing comprises four base extensions (4 repeats). For a field of view, a base base extension involves one image acquisition, with the fifth image and the sixth image being acquired from the same field of view of different base extensions. As such, the reference image obtained by processing and collecting information from the fifth image and the sixth image is used as a basis for correction, which can facilitate more accurate image correction.

In another example, two of the substrates (nucleotide analogues) corresponding to four types of bases used in a single-molecule two-color sequencing reaction contain one fluorescent dye and the other two substrates contain another fluorescent dye with a different excitation wavelength. One cycle of sequencing comprises two base extensions, and the two base substrates with different dyes are subjected to a binding reaction in a base base extension. For a field of view, a base extension involves two image acquisitions at different excitation wavelengths, with the fifth image and the sixth image respectively acquired from the same field of view of different base extensions or the same field of view at different excitation wavelengths of the same base extension. As such, the reference image obtained by processing and collecting information from the fifth image and the sixth image is used as a basis for correction, which can facilitate more accurate image correction.

In yet another example, one cycle of sequencing comprises one base extension, such as a two-color sequencing reaction on a second generation sequencing platform, in which substrates (such as nucleotide analogues) corresponding to four types of bases contain dye a, dye b, dye a and dye b, and no dye, respectively, with the dye a and the dye b having different excitation wavelengths. The four types of substrates enable one cycle of sequencing in the same base extension, with the fifth image and the sixth image respectively acquired from the same field of view of different sequencing reactions or the same field of view at different excitation wavelengths of the same sequencing reaction. As such, the reference image obtained by processing and collecting information from the fifth image and the sixth image is used as a basis for correction, which can facilitate more accurate image correction.

The fifth image and/or the sixth image may be either one image or a plurality of images. In one example, the fifth image is the first image, and the sixth image is the second image. Further, in some specific embodiments, constructing the reference image further comprises utilizing a seventh image and an eighth image. The image to be registered, the fifth image, the sixth image, the seventh image and the eighth image are acquired from the same field of view of a sequencing reaction, the fifth image, the sixth image, the seventh image and the eighth image respectively corresponding to fields of view during the base extensions of the four types of bases A, T/U, G and C. A plurality of nucleic acid molecules with an optically detectable label are present in this field of view during the base extension, and at least part of the nucleic acid molecules are present as spots in the images. Constructing the reference image further comprises: performing a coarse registration for the seventh image based on the fifth image, comprising: determining an offset between the seventh image and the fifth image, and moving the seventh image based on the offset to give a seventh image having undergone the coarse registration; performing a coarse registration for the eighth image based on the fifth image, comprising: determining an offset between the eighth image and the fifth image, and moving the eighth image based on the offset to give an eighth image having undergone the coarse registration; and merging the fifth image with the sixth image having undergone the coarse registration, the seventh image having undergone the coarse registration and the eighth image having undergone the coarse registration to give the reference image.

The embodiments of the present disclosure do not limit how the first registration is implemented. For example, Fourier transform can be used to determine the first offset by frequency domain registration. Specifically, for example, the first offset, the offset between the sixth image and the fifth image, the offset between the seventh image and the fifth image and/or the offset between the eighth image and the fifth image can be determined by referring to two-dimensional discrete Fourier transform in phase-only correlation function in Kenji TAKITA et al., *IEICE TRANS. FUNDAMENTALS*, VOL. E86-A, NO.8 AUGUST 2003. The first registration/coarse registration can reach a precision of 1 pixel. Thus, the first offset can be quickly and accurately determined and/or a reference image that facilitates precise correction can be constructed.

In some embodiments, the reference image and the image to be registered are binary images, which facilitates reduction of operation and quick correction.

In one example, both the image to be corrected and the reference image are binary images That is, each pixel in the images is either a or b, for example, a is 1 and b is 0, and the pixels labeled 1 are brighter or more intense than the pixels labeled 0. The reference image is constructed with the images acquired from four base extensions repeat1, repeat2, repeat3 and repeat4 in a cycle of sequencing, and the fifth image and the sixth image are selected from any one, two or three of the images repeat1-4.

In one example, the fifth image is the image repeat1, and the images repeat2, repeat3 and repeat4 are the sixth images. Images repeat2-4 are subjected to a coarse registration successively based on the image repeat1 to give images repeat2-4 having undergone the coarse registration respectively; and then the image repeat1 is merged with the images repeat 2-4 having undergone the coarse registration to give the reference image. The merging image is an overlap spot on the merging image. Based primarily on the size of spots of the corresponding nucleic acid molecules and the resolution of an imaging system, in one example, two spots distanced by no more than 1.5 pixels on two images are set as an overlap spot. Here, the central area of a composite image from images of 4 repeats is used as a reference image, which allows the reference image to have enough spots for subsequent registration, and allows information about spots in the detected and located center area to be relatively more accurate for accurate registration.

Figures 3, 4, 5:
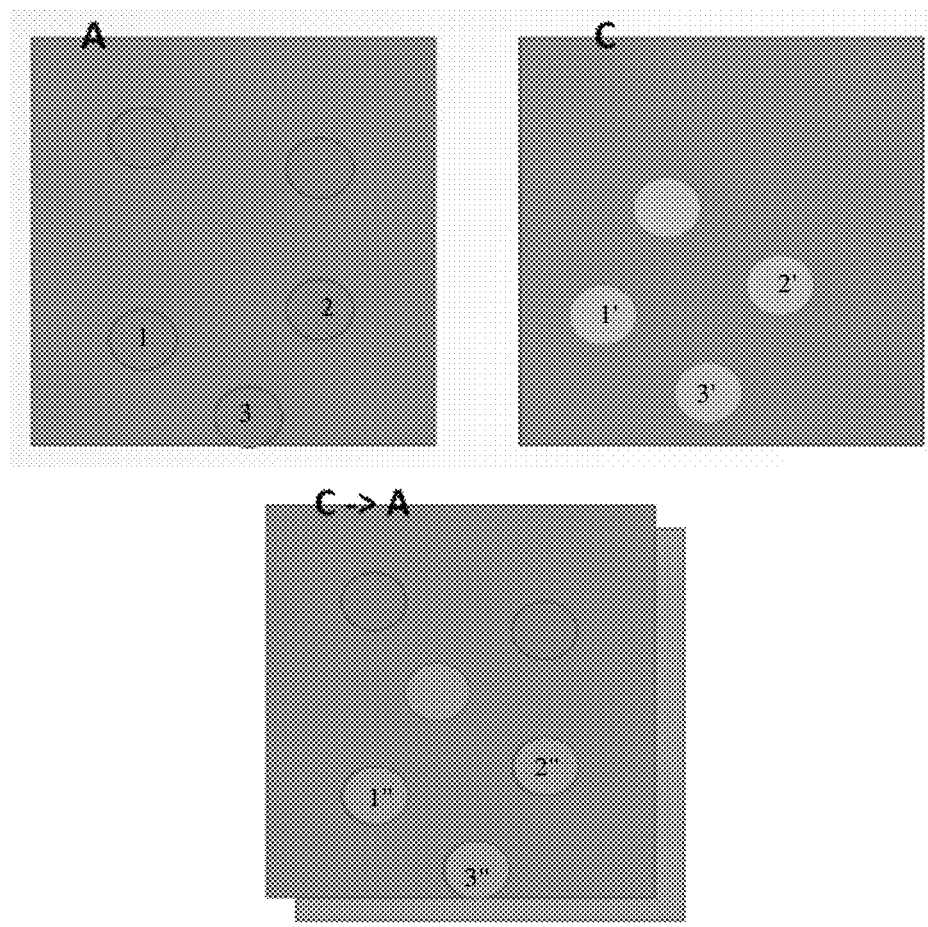
FIG. 3 is a schematic of a correction process and a correction result according to a specific embodiment of the present disclosure.
FIG. 4 is a schematic of a matrix corresponding to a candidate spot and pixel connectivity according to a specific embodiment of the present disclosure.
FIG. 5 is a schematic of pixel values in an area of m1×m2 centered on a center pixel of a pixel matrix according to a specific embodiment of the present disclosure.

In one example, the steps below are followed for image correction: 1) performing a coarse correction for an image repeat5 acquired from a field of view of a base extension of another cycle of sequencing, wherein the image repeat5 is a binarized image, the central area such as 512×512 area of the image and a central area of composite image from images repeat1-4 (an 512×512 area at the center of the corresponding reference image) are subjected to two-dimensional discrete Fourier transform to give an offset (x0,y0) by frequency domain registration, that is, to complete coarse image registration, with x0 and y0 reaching an precision of 1 pixel; 2) merging the image having undergone the coarse registration with the reference image based on spots on the images, comprising: calculating an offset (x1,y1) of the overlap spots in the central area of the image repeat5 and the corresponding area of the reference image according to the equation offset (x1,y1)=coordinate position of the spot on the image to be corrected—coordinate position of the corresponding spot on the reference image, which can be expressed as offset (x1,y1)=curRepeatPoints—basePoints; and calculating an average offset of all overlap spots to give the fine offset ranging from [0,0] to [1,1]. In one example, two spots distanced by no more than 1.5 pixels on two images are set as one overlap spot. 3) To sum up, an offset (x0,y0)-(x1,y1) for different cycles in a field of view (fov) is obtained, which for a spot (peak) can be expressed as:

curRepeatPoints+(x0,y0)−(x1,y1), where curRepeatPoints represents the original coordinates of the spot, that is, coordinates in the image before correction. The correction results from the above image correction have high accuracy, and the correction precision is less than or equal to 0.1 pixel. FIG. 3 illustrates the correction process and results. In FIG. 3, an image C is corrected based on an image A, circles in the images A and C represent spots, and spots with the same numerical symbols are overlap spots, and image C→A represents the correction result, that is, the result of aligning the image C to the image A.

The embodiments of the present disclosure do not limit the method for identifying and detecting spots on images. In some specific embodiments, performing image registration further comprises identifying a spot, comprising: detecting spots for an image using k1×k2 matrices, determining that the matrix in which a center pixel value of the matrix is not less than any non-center pixel value of the matrix corresponds to a candidate spot, and determining whether the candidate spot is the spot, wherein both k1 and k2 are odd numbers greater than 1, and the k1×k2 matrix comprises k1×k2 pixels. The image is selected from at least one of the image to be registered and the images for constructing the reference image. Spots (or peaks) on an image (particularly an image acquired from a nucleic acid sequence determination reaction) can be detected quickly and effectively by this method. There is no special limitation on the image to be detected, or original input data. The method is applicable to processing and analysis of any images generated by a nucleic acid sequencing platform based on optical detection, including but not limited to second- and third-generation sequencing, and features high accuracy and high efficiency and more information about the sequence acquired from the image. Specifically, for a random image and signal identification requiring high accuracy, the method has special advantages.

In some embodiments, the image is acquired from a nucleic acid sequence determination reaction, and nucleic acid molecules have optically detectable labels, e.g. fluorescent labels. The fluorescent molecules can be excited under the irradiation of laser with a specific wavelength to emit fluorescence, and the image is acquired by the imaging system. The acquired image contains peaks/spots which may correspond to the positions of the fluorescent molecules. It can be understood that at a focal plane position, the spots corresponding to the positions of the fluorescent molecules in the acquired image are smaller and brighter; and at a non-focal plane position, the spots corresponding to the positions of the fluorescent molecules in the acquired image are larger and darker. In addition, other substances/information which are not targeted or are hard to utilize later, such as impurities, may exist in a field of view; and further, as the field of view of a single molecule is photographed, a large number of molecule aggregates (clusters) will also interfere with the acquisition of target single molecule information. The single molecule is a few molecules, for example, the number of molecules is not greater than 10, e.g., 1, 2, 3, 4, 5, 6, 8 or 10.

In some examples, the center pixel value of the matrix is greater than a first preset value, any non-center pixel value of the matrix is greater than a second preset value, and the first preset value and the second preset value are related to an average pixel value of the image.

In some embodiments, the k1×k2 matrix can be used to perform traversal detection on the image, and the setting of the first preset value and/or the second preset value is related to the average pixel value of the image. For a grayscale image, the pixel value refers to the grayscale value. In the k1×k2 matrix, k1 and k2 may or may not be equal. In one example, related parameters of an imaging system includes: a 60× magnification for an objective lens, a size of 6.5 μm for an electronic sensor, the smallest identifiable size of 0.1 μm for a microscopic image acquired by the electronic sensor, a 16-bit grayscale or color image of 512×512, 1024×1024 or 2048×2048 for an output or input image, and a range of greater than 1 to less than 10 for k1 and k2. In one example, k1=k2=3; and in another example, k1=k2=5. For a color image having three pixel values for each pixel, the color image may be converted into a grayscale image before detecting the spots, so as to reduce the calculation and complexity in an image detection process. A non-grayscale image may be converted into a grayscale image with methods including but not limited to floating point algorithm, integer method, shift method, mean value method, etc.

In one example, based on a large number of image processing statistics, the first preset value is set as 1.4 times the average pixel value of the image, the second preset value is set as 1.1 times the average pixel value of the image, and thereby, interference can be eliminated and a spot detection result can be obtained from optically detectable labels.

Candidate spots can be further screened and determined by size, degree of similarity with an ideal spot, and/or intensity. In some specific embodiments, the size of a candidate spot on the image is quantitatively reflected and compared by the size of connected component corresponding to the candidate spot, so as to screen and determine whether the candidate spot is a spot needed.

In one example, determining whether a candidate spot is a spot comprises: calculating the size of a connected component corresponding to a candidate spot according to the equation Area=A×B, and determining the candidate spot with the size of corresponding connected component greater than a third preset value as the spot, wherein A represents the size of the pixel connectivity in a row where the center of a matrix corresponding to the candidate spot is located, B represents the size of the pixel connectivity in a column where the center of the matrix corresponding to the candidate spot is located, and a pixel connectivity in the k1×k2 matrix which is greater than an average pixel value is defined as the connected component corresponding to the candidate spot. As such, spots which correspond to labeled molecules and are applicable for subsequent sequence identification can be effectively obtained, so that nucleic acid sequence information can be obtained.

In one example, based on the average pixel value of the image, two or more adjacent pixels which are not less than the average pixel value is the pixel connectivity. As shown in FIG. 4, the bold and enlarged part represents the center of the matrix corresponding to the candidate spot; the thick frame represents the 3×3 matrix corresponding to the candidate spot; the pixels marked as 1 are pixels which are not less than the average pixel value of the image; and the pixels marked as 0 are pixels which are less than the average pixel value. It can be seen that A=3 and B=6, so the size of the connected component corresponding to the candidate spot is A×B=3×6.

The third preset value can be determined according to the sizes of connected components corresponding to all the candidate spots on the image. For example, by calculating the size of a connected component corresponding to each candidate spot on the image, the average size of the connected components corresponding to the spots, which represents a feature of the image, is taken as a third preset value. For another example, the sizes of the connected components corresponding to the candidate spots on the image can be sorted in ascending order, and the size of the connected component at the 50th, 60th, 70th, 80th or 90th percentile is taken as the third preset value. As such, spot information can be obtained effectively, which is favorable for subsequent nucleic acid sequence identification.

In some examples, the intensities of candidate spots are quantitatively reflected and compared by statistically analyzing setting parameters, so as to screen the candidate spots. In one example, determining whether a candidate spot is a spot comprises: calculating score of a candidate spot according to the equation Score=$((k1 \times k2-1)CV-EV)/((CV+EV)/(k1 \times k2))$, and determining the candidate spot with the score greater than a fourth preset value as the spot, wherein CV represents the center pixel value of a matrix corresponding to the candidate spot, and EV represents the sum of non-center pixel values of the matrix corresponding to the spot. As such, spots which correspond to labeled molecules and are applicable for subsequent sequence identification can be effectively obtained, so that nucleic acid sequence information can be obtained.

The fourth preset value can be determined according to the scores of all the candidate spots on the image. For example, when the number of the candidate spots on the image is greater than a certain number which meets a statistic requirement for quantity, for example, the number of the candidate spots on the image is greater than 30, the scores of all the candidate spots of the image can be calculated and sorted in ascending order, and the fourth preset value can be set as a score at the 50th, 60th, 70th, 80th or 90th quantile. As such, the candidate spots with scores less than the score at the 50th, 60th, 70th, 80th or 90th quantile can be discarded, so that target spots can be obtained effectively, which is favorable for subsequent accurate base sequence identification. The basis of this processing or screening setting is that generally a concentrated spot with great difference in intensity/pixel value between the center and the edge is considered to be a spot corresponding to the position of a molecule to be detected. In general, the number of candidate spots on an image is greater than 50, 100 or 1000.

In some examples, candidate spots are screened according to morphology and intensity/brightness. In one example, determining whether a candidate spot is a spot comprises: calculating the size of a connected component corresponding to a candidate spot according to the equation Area=$A \times B$, and calculating the score of the candidate spot according to the equation Score=$((k1 \times k2-1)CV-EV)/((CV+EV)/(k1*k2))$, wherein A represents the size of the pixel connectivity in a row where the center of a matrix corresponding to the candidate spot is located, B represents the size of the pixel connectivity in a column where the center of the matrix corresponding to the candidate spot is located, a pixel connectivity in the $k1 \times k2$ matrix which is greater than an average pixel value is defined as the connected component corresponding to the candidate spot, CV represents the center pixel value of a matrix corresponding to the candidate spot, and EV represents the sum of non-center pixel values of the matrix corresponding to the spot; and determining the candidate spot with the size of corresponding connected component greater than a third preset value and the score greater than a fourth present value as the spot. As such, spot information which corresponds to nucleic acid molecules and is favorable for subsequent sequence identification can be obtained effectively. The third preset value and/or the fourth preset value can be considered and set by reference to aforementioned specific embodiments.

In some specific embodiments, the method for image registration also comprises identifying and detecting a spot, comprising: preprocessing an image to give a preprocessed image, wherein the image is at least one of a first image, a second image, a third image, a fourth image, a fifth image, a sixth image, a seventh image and an eighth image; determining a critical value to simplify the preprocessed image so as to give a simplified image, comprising: assigning a first preset value to a pixel value of a pixel on the preprocessed image less than the critical value and assigning a second preset value to a pixel value of a pixel on the preprocessed image not less than the critical value; determining a first spot detection threshold c1 based on the preprocessed image; identifying a candidate spot on the image based on the preprocessed image and the simplified image, comprising: determining a pixel matrix meeting at least two of the following conditions a)-c) as the candidate spot: a) in the preprocessed image, the center pixel of the pixel matrix has the maximum pixel value, the pixel matrix is represented by $r1 \times r2$, both r1 and r2 are odd numbers greater than 1, and the pixel matrix $r1 \times r2$ comprises $r1 \times r2$ pixels, b) in the simplified image, the pixel value of the center pixel of the pixel matrix is the second preset value, and the pixel connectivity in the pixel matrix is greater than $$\frac{2}{3} \times r1 \times r2,$$

and c) in the preprocessed image, the pixel value of the center pixel of the pixel matrix is greater than a third preset value, $g1 \times g2$ is $>c1$, g1 is a correlation coefficient of two-dimensional Gaussian distribution in an area of $m1 \times m2$ centered on the center pixel of the pixel matrix, g2 is a pixel matrix in the area of $m1 \times m2$, both m1 and m2 are odd numbers greater than 1, and the area of $m1 \times m2$ comprises $m1 \times m2$ pixels; and determining whether the candidate spot is the spot. Spots on an image (particularly an image acquired from a nucleic acid sequence determination reaction) can be detected quickly and effectively by this method, including using determining conditions or the combination thereof determined by a large amount of data training. There is no special limitation on the image to be detected, or original input data. The method is applicable to processing and analysis of any images generated by a nucleic acid sequencing platform based on optical detection, including but not limited to second- and third-generation sequencing, and features high accuracy and high efficiency and more information about the sequence acquired from the image. Specifically, for a random image and signal identification requiring high accuracy, the method has special advantages.

For a grayscale image, the pixel value refers to the grayscale value. For a color image having three pixel values for each pixel, the color image may be converted into a grayscale image before detecting the spots, so as to reduce the calculation and complexity in an image detection process. A non-grayscale image may be converted into a grayscale image with methods including but not limited to floating point algorithm, integer method, shift method, mean value method, etc.

In some embodiments, preprocessing the image comprises: determining a background of the image using opening operation; converting the image into a first image based on the background using top-hat operation; performing Gaussian blur on the first image to give a second image; and sharpening the second image to give the preprocessed image. In this way, noise of the image can be effectively reduced or the signal-to-noise ratio of the image can be improved, which helps to accurately detect a spot.

Opening operation is a morphological process, and specifically, a process of sequential expansion and corrosion. The corrosion reduces the foreground (a portion of interest), and the expansion enlarges the foreground. The opening operation can be used to eliminate small objects, separate objects at a fine point, and smooth the boundary of a large object without significantly changing its area. In this embodiment, the size of a structural element p1×p2 (a basic template used to process the image) for opening operation on the image is not specifically defined, and p1 and p2 are odd numbers. In one example, the structural element p1×p2 may be 15×15, 31×31, or the like, and finally a preprocessed image that is beneficial for subsequent processing and analysis can be obtained.

The top-hat operation is usually used to separate plaques that are brighter than neighboring points (peaks/spots). When an image has a large area of background and regular small items, the background may be extracted using top-hat operation. In one example, the top-hat transformation of an image comprises: performing the opening operation on the image, and subtracting the opening operation result from the original image to give a first image, i.e., the image given by the top-hat transformation. The mathematical expression of the top-hat transformation is dst=tophat(src,element)=src−open(src,element). The inventor believes that, the opening operation may enlarge cracks or blocks of low brightness. Therefore, subtracting opening operation result from the original image may highlight blocks brighter than surrounding blocks in the original image. The operation is related to the size of a selected kernel, in other words, related to an expected size of the peak/spot. If the peak has an unexpected size, the processing may lead to many small bumps on the whole image, a specific example of which may be a defocused image, i.e. messed and blurred peaks/spots. In one example, the expected size of the peak, or the size of the kernel, is 3×3, and the image acquired from the top-hat transformation is conducive to subsequent denoising process.

Gaussian blur, also referred to as Gaussian filter, is a linear smoothing filter applicable for eliminating Gaussian noise, and is widely used in denoising of image processing. Generally speaking, the Gaussian filter is a process of weighted averaging on the whole image. A value of each pixel is a weighted average of the value itself and other pixel values in neighborhood. The specific procedure of the Gaussian filter is: scanning each pixel in the image using a template (also referred to as convolution or mask), and replacing the value of the center pixel of the template with a weighted average grayscale value of pixels in neighborhood determined using the template. In one example, the Gaussian blur is performed on the first image using GaussianBlur function in OpenCV. The Gaussian distribution parameter Sigma is 0.9, and the two-dimensional filter matrix (convolution kernel) used is 3×3. From a perspective of an image, after the Gaussian blur, the small bumps on the first image are smoothed, and edges of the image are smooth. Further, the second image, or the image acquired from the Gaussian filter, is sharpened, for example, by two-dimensional Laplacian sharpening. From a perspective of an image, edges are sharpened after processing, and the image acquired from the Gaussian blur is restored.

In some embodiments, simplifying the preprocessed image comprises: determining a critical value based on the background and the preprocessed image; and comparing pixel values of pixels on the preprocessed image with the critical value so as to give a simplified image, comprising: assigning a first preset value to pixel values of the pixels on the preprocessed image less than the critical value and assigning a second preset value to the pixel values of the pixels on the preprocessed image not less than the critical value. As such, according to the critical value determining manner and the critical value determined by summarizing a large amount of data, the preprocessed image is simplified, for example, by binarization, which may facilitate subsequent accurate spot detection, accurate base identification, high-quality data acquisition, and the like.

Specifically, in some examples, acquiring a simplified image comprises: dividing the sharpening result obtained after preprocessing by an opening operation result to give a set of values corresponding to the pixels of the image; and determining a critical value of the pre-binarized image through this set of values. For example, the set of values may be sorted in ascending order, and the value at the 20th, 30th or 40th percentile in the set of values may serve as the binarization critical value/threshold. As such, the binary image may facilitate subsequent accurate detection and identification of spots.

In one example, the structural element for opening operation of image preprocessing is p1×p2, and the preprocessed image (the sharpening result) is divided by the opening operation result to give a set of arrays/matrices p1×p2 of the same size as the structural element. The p1×p2 values comprised in each array are sorted in ascending order, and the 30th percentile in the array serves as the binarization critical value/threshold of the block (numerical matrix). As such, a threshold is determined for binarization in each block of the image, and the final binarization result highlights required information while denoising, which facilitate subsequent accurate detection of spots.

In some examples, a first spot detection threshold is determined by Otsu's method. The Otsu's method (Otsu's algorithm) can also be referred to as a method of maximum inter-class variance that maximizes the inter-class variance to segment an image, which indicates fewer segmentation errors and high accuracy. It is assumed that the segmentation threshold of the foreground and the background of the preprocessed image is T(c1), the proportion of pixels in the foreground to the whole image is $w_0$ with the average grayscale value being $\mu_0$, and the proportion of pixels in the background to the whole image is $w_1$ with the average grayscale value being $\mu_1$. The overall average grayscale value of the image to be processed is denoted as $\mu$, and the inter-class variance is denoted as var, which are: $\mu=\omega_0*\mu_0+\omega_1*\mu_1$; $var=\omega_0(\mu_0-\mu)^2\omega_1(\mu_1-\mu)^2$. The latter is substituted into the former, getting the following equation: $var=\omega_0\omega_1(\mu_1-\mu_0)^2$. The segmentation threshold T that maximizes the inter-class variance is acquired by a traversal method, and it is the required first spot detection threshold c1.

In some embodiments, identifying a candidate spot on the image based on the preprocessed image and the simplified image comprises determining a pixel matrix fulfilling at least two of the conditions a)-c) as the candidate spot. As such, the accuracy of subsequent nucleic acid sequencing based on spot information and the quality of reads may be effectively improved.

Specifically, in one example, conditions required for determining a candidate spot include a), wherein k1 and k2 may or may not be equal. In one example, related parameters of an imaging system includes: a 60× magnification for an objective lens, a size of 6.5 μm for an electronic sensor, the smallest identifiable size of 0.1 μm for a microscopic image acquired by the electronic sensor, a 16-bit grayscale or color image of 512×512, 1024×1024 or 2048×2048 for an output or input image, and a range of greater than 1 to less than 10 for k1 and k2. In one example, in a preprocessed image, k1 and k2 are set at 3 according to the expected size of spot; and in another example, k1 and k2 are set at 5.

In one example, conditions required for determining a candidate spot include b), namely in the simplified image, the pixel value of the center pixel of the pixel matrix is the second preset value, and the pixel connectivity of the pixel matrix is greater than $$\frac{2}{3} \times k1 \times k2,$$

i.e., the pixel value of the center pixel is greater than the critical value, and the pixel connectivity is greater than two thirds of the matrix. Here, two or more pixels with adjacent pixel values equal to the second preset value are the pixel connectivity. For example, the simplified image is a binary image, the first preset value is 0, and the second preset value is 1. As shown in FIG. 4, the bold and enlarged part represents the center of a pixel matrix, and the thick frame represents the pixel matrix 3×3, that is, k1=k2=3. The pixel value of the center pixel of the matrix is 1, the pixel connectivity is 4, which is less than $$\frac{2}{3} \times k1 \times k2 = 6,$$

and therefore the pixel matrix does not meet the condition b), and is not a candidate spot.

In one example, conditions required for determining a candidate spot include c), wherein in the preprocessed image, g2 is a corrected pixel matrix in the area of m1×m2, e.g. a sum of corrected pixels in the area of m1×m2. In one example, correction is performed according to the proportion of the pixels with pixel values equal to the second present value in the corresponding area of m1×m2 in the simplified image. For example, as shown in FIG. 5, m1=m2=5, the proportion of the pixels with pixel values equal to the second present value in the corresponding area of m1×m2 in the simplified image is 13/25 (13 "1"s), and corrected g2 is 13/25 of original g2. As such, it facilitates accuracy of the spot detection and identification, and subsequent analysis and interpretation of spot information.

In some examples, determining whether a candidate spot is a spot also comprises: determining a second spot detection threshold based on the preprocessed image, and determining a candidate spot with a pixel value not less than the second spot detection threshold as a spot. In one specific example, a pixel value of a pixel to which the coordinates of the candidate spot correspond is assigned to the pixel value of the candidate spot. After the candidate spots are further screened using the second spot detection threshold determined based on the preprocessed image, at least a part of spots that are more likely the image background but are similar to "spots" in brightness (intensity) and/or shape may be excluded, which helps to accurately identify a sequence based on the spot, and improves quality of reads.

In one example, the coordinates of the candidate spot, including sub-pixel coordinates, may be given by centroid method. The grayscale value of the coordinates of the candidate spot is calculated by bilinear interpolation.

In some specific examples, determining whether a candidate spot is a spot comprises: dividing the preprocessed image into a set of blocks of a predetermined size, and sorting the pixel values of pixels in the block to determine the second spot detection threshold corresponding to the block; and determining a candidate spot in the block with a pixel value not less than the second spot detection threshold corresponding to the block as a spot. As such, a difference between different blocks of the image such as an overall difference of light intensity is distinguished, and each spot is further detected and identified, so as to help to accurately identify the spot and find more spots.

When dividing the preprocessed image into a set of block of a predetermined size, the blocks may or may not overlap with each other. In one example, the blocks do not overlap with each other. In some embodiments, the size of the preprocessed image is not less than 512×512, such as 512×512, 1024×1024, 1800×1800, or 2056×2056, and the block of the predetermined size may be set as 200×200. As such, the spot is quickly calculated, determined, and identified.

Figure 6:
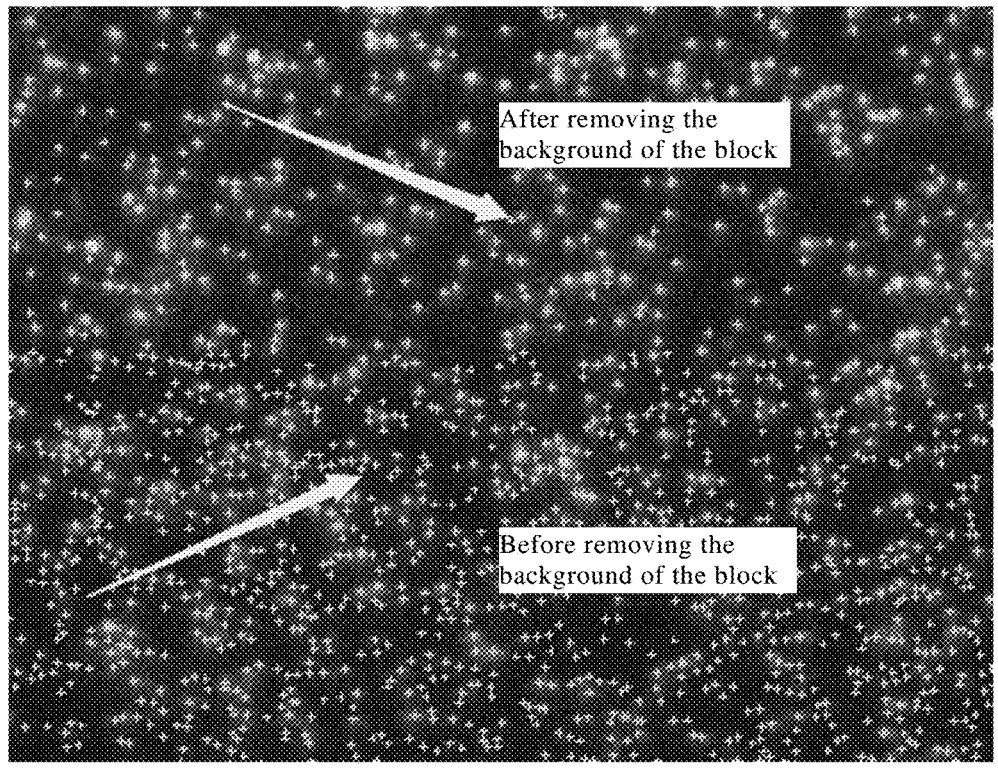
FIG. 6 is a schematic showing the comparison between spot detection results obtained before and after determination based on a second spot detection threshold according to a specific embodiment of the present disclosure.

In some embodiments, when determining a second spot detection threshold corresponding to the block, pixel values of pixels in each block are sorted in ascending order. The p10+(p10−p1)×4.1 is used as the second spot detection threshold corresponding to the block, i.e., a background of the block, where p1 represents the first percentile, and p10 represents the tenth percentile. The threshold is a relatively stable threshold determined by a large amount of data training, which can eliminate a majority of spots on the background. It can be understood that when an optical system is adjusted and overall pixel distribution of the image changes, the threshold may need appropriate adjustment. FIG. 6 is a schematic showing the comparison between spot detection results obtained before and after the processing, i.e. a schematic showing spot detection results before and after removing the background of a block. The upper half of FIG. 6 is the spot detection result after the processing, the lower half is the spot detection result before the processing, and the cross marks are candidate spots or spots.

One embodiment of the present disclosure also provides a base calling method, comprising: matching spots on images acquired from a base extension of a base to a spot set corresponding to a sequencing template, and performing base calling according to the matched spots, wherein a plurality of nucleic acid molecules with an optically detectable label are present in the field of view corresponding to the images acquired from the base extension, at least part of the nucleic acid molecules are present as spots in the images acquired from the base extension, and the spot set corresponding to the sequencing template is constructed by the method for constructing a sequencing template based on images according to any of the aforementioned embodiments of the present disclosure.

The aforementioned description of the technical features and advantages of the method for constructing a sequencing template based on images in any of the embodiments is also applicable to the base calling method in this embodiment of the present disclosure, and will not be repeated herein.

Specifically, the spots in the images acquired from the base extension can be matched with the constructed spot set in a traversal manner. In some specific embodiments, if a distance between any spot in the spot set corresponding to the sequencing template and any spot on the images acquired from the base extension is less than a third predetermined pixel, it is determined that the spot on the images acquired from the base extension matches the spot set corresponding to the sequencing template. In one example, the third predetermined pixel is 2. Thus, accurate base calling can be fulfilled, and part of the base sequence (reads) of a template can be obtained.

Logic and/or steps shown in the flowcharts or described herein in other manners, for example, may be considered as a program list of executable instructions that are used to implement logical functions, and may be specifically implemented on any computer-readable storage medium, for an instruction execution system, device, or apparatus (for example, a computer-based system, a system including a processor, or another system that can fetch instructions from the instruction execution system, apparatus, or device and execute the instructions), or for a combination of the instruction execution system, device or apparatus. As used herein, the "computer-readable storage medium" may be any device that may include, store, communicate, propagate, or transmit a program for an instruction execution system, device, or apparatus, or for a combination of the instruction execution system, device, or apparatus. More specific examples (this list is not exhaustive) of the computer-readable storage medium include the following: an electrical connection (an electrical device) with one or more buses, a portable computer cartridge (an magnetic device), a random-access memory (RAM), a read-only memory (ROM), an erasable programmable read-only memory (EPROM or flash memory), an optical fiber device, and a portable compact disc read-only memory (CDROM). In addition, the computer-readable storage medium may even be a piece of paper on which the programs can be printed or any other appropriate media, because, for example, the paper or the media may be optically scanned, and the program may be electrically acquired by processing such as edition, decoding, or any other appropriate means when necessary and then stored in a computer storage.

Figure 7:
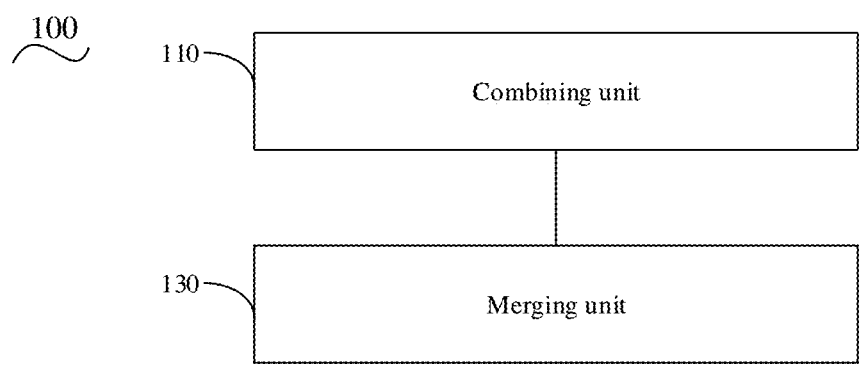
FIG. 7 is a structural schematic of a device for constructing a sequencing template based on images according to a specific embodiment of the present disclosure.

One embodiment of the present disclosure also provides a device 100 (as shown in FIG. 7) for constructing a sequencing template based on images, which is used to implement the method for constructing a sequencing template based on images according to any of the aforementioned embodiments of the present disclosure. The images comprise a first image, a second image, a third image and a fourth image of the same field of view respectively corresponding to base extensions of four types of bases A, T/U, G and C. A plurality of nucleic acid molecules with an optically detectable label are present in this field of view during the base extensions, and at least part of the nucleic acid molecules are present as spots in the images Sequential and/or simultaneous completion of the base extensions of the four types of bases once is defined as one cycle of sequencing. The first image comprises an image M1 and an image M2, the second image comprises an image N1 and an image N2, the third image comprises an image P1 and an image P2, and the fourth image comprises an image Q1 and an image Q2. The images M1 and M2 respectively come from two cycles of sequencing, the images N1 and N2 respectively come from two cycles of sequencing, the images P1 and P2 respectively come from two cycles of sequencing, and the images Q1 and Q2 respectively come from two cycles of sequencing. The device comprises: a combining unit 110 configured for combining any two of the images M1, M2, N1, N2, P1, P2, Q1 and Q2 for spot matching, such that the images M1, M2, N1, N2, P1, P2, Q1 and Q2 each participate in at least one combination to give a plurality of combination images each comprising a first overlap spot, with two or more spots distanced by less than a first predetermined pixel on a combination image being defined as a first overlap spot; and a merging unit 130 configured for merging the first overlap spots on the plurality of combination images to give a spot set corresponding to the sequencing template.

The aforementioned description of the technical features and advantages of the method for constructing a sequencing template based on images in any of the embodiments of the present disclosure is also applicable to the device 100 in this embodiment of the present disclosure, and will not be repeated herein. For example, in the merging unit 130, merging the first overlap spots on the plurality of combination images comprises: performing one or more matchings between the first overlap spots on different combination images to give the spot set corresponding to the sequencing template.

In some examples, the images M1, N1, P1 and Q1 are sequentially acquired, and the images M2, N2, P2 and Q2 are sequentially acquired. The combining unit 130 is configured for combining the images M1, M2, N1, N2, P1, P2, Q1 and Q2 in pairs at an interval of S images to give K combination images, and discarding non-overlap spots on the combination images by matching spots on the combination images, wherein S is an integer from 0 to $S_{max}$, and $S_{max}$=total number of images participating in combination−4, and k=((the total number of images participating in combination−S−1)+1)×(the total number of images participating in combination−S−1)/2.

In some examples, the images are registered images.

Specifically, the device 100 also comprises a registration unit 108 configured for image registration. The registration unit comprises a first registration module and a second registration module. The first registration module is configured for: performing a first registration for an image to be registered based on a reference image, wherein the reference image and the image to be registered correspond to the same field of view, comprising: determining a first offset between a predetermined region on the image to be registered and a corresponding predetermined region on the reference image, and moving all spots on the image to be registered based on the first offset to give an image to be registered having undergone the first registration. The second registration module is configured for: performing a second registration for the image to be registered having undergone the first registration based on the reference image, comprising: merging the image to be registered having undergone the first registration with the reference image to give a merging image, calculating an offset of all second overlap spots in a predetermined region on the merging image to determine a second offset, with two or more spots distanced by less than a second predetermined pixel being defined as a second overlap spot, and moving all spots on the image to be registered having undergone the first registration based on the second offset to register the image to be registered.

In some examples, the reference image is acquired by construction, and the registration unit 108 also comprises a reference image construction module, which is configured for: acquiring a fifth image and a sixth image corresponding to the same field as the image to be registered; performing a coarse registration for the sixth image based on the fifth image, comprising: determining an offset between the sixth image and the fifth image, and moving the sixth image based on the offset to give a sixth image having undergone the coarse registration; and merging the fifth image with the sixth image having undergone the coarse registration to give the reference image.

In some examples, utilizing the reference image construction module to construct the reference image also comprises utilizing a seventh image and an eighth image, wherein the seventh image and the eighth image are acquired from the same field of view of sequencing reaction as the image to be registered, the fifth image, the sixth image, the seventh image and the eighth image respectively corresponding to fields of view during the base extensions of the four types of bases A, T/U, G and C. Constructing the reference image further comprises: performing a coarse registration for the seventh image based on the fifth image, comprising: determining an offset between the seventh image and the fifth image, and moving the seventh image based on the offset to give a seventh image having undergone the coarse registration; performing a coarse registration for the eighth image based on the fifth image, comprising: determining an offset between the eighth image and the fifth image, and moving the eighth image based on the offset to give an eighth image having undergone the coarse registration; and merging the fifth image with the sixth image having undergone the coarse registration, the seventh image having undergone the coarse registration and the eighth image having undergone the coarse registration to give the reference image.

In some examples, the reference image and the image to be registered are binary images.

In some examples, two-dimensional discrete Fourier transform is employed to determine the first offset, the offset between the sixth image and the fifth image, the offset between the seventh image and the fifth image, and/or the offset between the eighth image and the fifth image.

In some examples, the device 100 also comprises a spot detection unit 106, which is configured for: preprocessing an image to give a preprocessed image; determining a critical value to simplify the preprocessed image so as to give a simplified image, comprising: assigning a first preset value to a pixel value of a pixel on the preprocessed image less than the critical value and assigning a second preset value to a pixel value of a pixel on the preprocessed image not less than the critical value; determining a first spot detection threshold c1 based on the preprocessed image; identifying a candidate spot on the image based on the preprocessed image and the simplified image, comprising: determining a pixel matrix meeting at least two of the following conditions a)-c) as a candidate spot: a) in the preprocessed image, the center pixel of the pixel matrix has the maximum pixel value, the pixel matrix is represented by k1×k2, both k1 and r2 are odd numbers greater than 1, and the pixel matrix k1×k2 comprises k1×k2 pixels, b) in the simplified image, the pixel value of the center pixel of the pixel matrix is the second preset value, and the pixel connectivity in the pixel matrix is greater than ⅔×k1×k2, and c) in the preprocessed image, the pixel value of the center pixel of the pixel matrix is greater than a third preset value, g1×g2 is >c1, g1 is a correlation coefficient of two-dimensional Gaussian distribution in an area of m1×m2 centered on the center pixel of the pixel matrix, g2 is a pixel matrix in the area of m1×m2, both m1 and m2 are odd numbers greater than 1, and the area of m1×m2 comprises m1×m2 pixels.

In some examples, the spot detection unit 106 is also configured for determining whether a candidate spot is a spot, comprising: determining a second spot detection threshold based on the preprocessed image, and determining a candidate spot with a pixel value not less than the second spot detection threshold as a spot. In some examples, the pixel value of the candidate spot is the pixel value of a pixel to which coordinates of the candidate spot correspond.

In some examples, in the spot detection unit 106, determining whether a candidate spot is a spot comprises: dividing the preprocessed image into a set of blocks of a predetermined size, sorting pixels in the block by pixel value to determine the second spot detection threshold corresponding to the block, and determining a candidate spot in the block with a pixel value not less than the second spot detection threshold corresponding to the block as a spot.

In some examples, in the spot detection unit 106, preprocessing the image comprises: determining a background of the image using opening operation, converting the image into a first image based on the background using top-hat operation, performing Gaussian blur on the first image to give a second image; and sharpening the second image to give the preprocessed image.

In some examples, in the spot detection unit 106, determining a critical value to simplify the preprocessed image so as to give a simplified image comprises: determining a critical value based on the background and the preprocessed image, and comparing pixel values of pixels on the preprocessed image with the critical value so as to give a simplified image.

In some examples, g2 is a corrected pixel matrix in the area of m1×m2, and the correction is performed based on the proportion of pixels with the second preset pixel value in the corresponding area of m1×m2 in the simplified image.

One embodiment of the present disclosure also provides a device for base calling 1000 configured for implementing the method for base calling according to any of the aforementioned specific embodiments of the present disclosure. The device 1000 is configured for: matching spots on images acquired from a base extension of a base to a spot set corresponding to a sequencing template, and performing base calling according to the matched spots, wherein a plurality of nucleic acid molecules with an optically detectable label are present in the field of view corresponding to the images acquired from the base extension, at least part of the nucleic acid molecules are present as spots in the images acquired from the base extension, and the spot set corresponding to the sequencing template is constructed by the method and/or device for constructing a sequencing template based on images according to any of the aforementioned embodiments of the present disclosure.

Specifically, in the device for base calling 1000, if a distance between any spot in the spot set corresponding to the sequencing template and any spot on the images acquired from the base extension is less than a third predetermined pixel, it is determined that the spot on the images acquired from the base extension matches the spot set corresponding to the sequencing template.

According to one embodiment of the present disclosure, a computer program product comprising an instruction for implementing the instruction of a sequencing template based on images is also provided, wherein the instruction causes a computer to execute the method for constructing a sequencing template based on images according to any of the aforementioned specific embodiments of the present disclosure when the program is executed by the computer.

According to one embodiment of the present disclosure, another computer program product comprising an instruction for base calling is also provided, wherein the instruction causes a computer to execute the method for base calling according to any of the aforementioned embodiments of the present disclosure when the program is executed by the computer.

It will be appreciated by those skilled in the art know that, in addition to implementing the controller/processor in a form of computer-readable program code, same functions can be implemented in a form of a logic gate, a switch, an application-specific integrated circuit, an editable logic controller, an embedded microcontroller, and the like by logically programming the steps. Therefore, the controller/processor may be regarded as a hardware component, and a device included in the controller/processor for implementing various functions may also be regarded as a structure in the hardware component. Alternatively, a device for implementing various functions may be regarded as both a software module for implementing the method and a structure in the hardware component.

In the specification, descriptions such as "one embodiment", "some embodiments", "one or some specific embodiments", "one or some examples" or the like, mean that a particular feature, structure or characteristic described in reference to the embodiment or example is included in at least one embodiment or example of the present disclosure. In this specification, the schematic description of the aforementioned terms do not necessarily refer to the same embodiment or example. Moreover, the specific features, structures and other characteristics described may be combined in any one or more embodiments or examples in an appropriate manner.

Although the embodiments of the present disclosure have been illustrated and described, it can be understood by those of ordinary skill in the art that various changes, modifications, replacements and variations can be made to these embodiments without departing from the principle and purpose of the present disclosure, and the scope of the present disclosure is defined by the claims and equivalents thereof.

What is claimed is:

1. A method for constructing a sequencing template based on images, wherein the images comprise a first image, a second image, a third image and a fourth image of the same field of view respectively corresponding to base extensions of four types of bases A, T/U, G and C; a plurality of nucleic acid molecules with optically detectable labels are present in the field of view during the base extensions, and at least part of the nucleic acid molecules are present as spots on the images; sequential and/or simultaneous completion of the base extensions of the four types of bases is defined as one cycle of sequencing;

the first image comprises an image M1 and an image M2, the second image comprises an image N1 and an image N2, the third image comprises an image P1 and an image P2, and the fourth image comprises an image Q1 and an image Q2;

the images M1 and M2 respectively come from two cycles of sequencing, the images N1 and N2 respectively come from two cycle of sequencing, the images P1 and P2 respectively come from two cycles of sequencing, and the images Q1 and Q2 respectively come from two cycles of sequencing; and the method comprises:

combining any two of the images M1, M2, N1, N2, P1, P2, Q1 and Q2 for spot matching, such that the images M1, M2, N1, N2, P1, P2, Q1 and Q2 each participate in at least one combination to give a plurality of combination images each comprising a first overlap spot, with two or more spots distanced by less than a first predetermined pixel on a combination image being defined as a first overlap spot; and merging the first overlap spots on the plurality of combination images to give a spot set corresponding to the sequencing template.

2. The method according to claim 1, wherein merging the first overlap spots on the plurality of combination images comprises: performing one or more matchings between the first overlap spots on different combination images to give the spot set corresponding to the sequencing template.

3. The method according to claim 1, wherein the images M1, N1, P1 and Q1 are sequentially acquired, and the images M2, N2, P2 and Q2 are sequentially acquired; and combining any two of the images M1, M2, N1, N2, P1, P2, Q1 and Q2 for spot matching, such that the images M1, M2, N1, N2, P1, P2, Q1 and Q2 each participate in at least one combination to give a plurality of combination images each comprising a first overlap spot, comprises:

combining the images M1, M2, N1, N2, P1, P2, Q1 and Q2 in pairs at an interval of S images to give K combination images, and discarding non-overlap spots on the combination images by matching spots on the combination images, wherein S is an integer from 0 to $S_{max}$, and $S_{max}$=total number of images participating in combination 4.

4. The method according to claim 1, wherein the images are registered images.

5. The method according to claim 4, wherein registering the images comprises:

performing a first registration for an image to be registered based on a reference image, wherein the reference image and the image to be registered correspond to the same field of view, comprising:

determining a first offset between a predetermined region on the image to be registered and a corresponding predetermined region on the reference image, and moving all spots on the image to be registered based on the first offset to give an image to be registered having undergone the first registration; and performing a second registration for the image to be registered having undergone the first registration based on the reference image, comprising:

merging the image to be registered having undergone the first registration with the reference image to give a merging image;

calculating an offset of second overlap spots in a predetermined region on the merging image to determine a second offset, two or more spots distanced by less than a second predetermined pixel on the merging image being defined as a second overlap spot; and moving all spots on the image to be registered having undergone the first registration based on the second offset to register the image to be registered.

6. The method according to claim 5, wherein the reference image is acquired by construction, and constructing the reference image comprises:

acquiring a fifth image and a sixth image corresponding to the same field of view as the image to be registered;

performing a coarse registration for the sixth image based on the fifth image, comprising: determining an offset between the sixth image and the fifth image, and moving the sixth image based on the offset to give a sixth image having undergone the coarse registration; and merging the fifth image with the sixth image having undergone the coarse registration to give the reference image.

7. The method according to claim 6, wherein constructing the reference image further comprises: using a seventh image and an eighth image acquired from the same field of view of sequencing as the image to be registered, the fifth image, the sixth image, the seventh image and the eighth image respectively corresponding to the fields of view during the base extensions of the four types of bases A, G and C; and constructing the reference image further comprises:

performing a coarse registration for the seventh image based on the fifth image, comprising: determining an offset between the seventh image and the fifth image, and moving the seventh image based on the offset to give a seventh image having undergone the coarse registration;

performing a coarse registration for the eighth image based on the fifth image, comprising: determining an offset between the eighth image and the fifth image, and moving the eighth image based on the offset to give an eighth image having undergone the coarse registration; and merging the fifth image with the sixth image having undergone the coarse registration, the seventh image having undergone the coarse registration and the eighth image having undergone the coarse registration to give the reference image.

8. The method according to claim 5, wherein the reference image and the image to be registered are binary images.

9. The method according to claim 5, wherein two-dimensional discrete Fourier transform is employed to determine the first offset.

10. The method according to claim 1, further comprising: detecting the spots on an image, comprising:

preprocessing the image to give a preprocessed image;

determining a critical value to simplify the preprocessed image so as to give a simplified image, comprising: assigning a first preset value to a pixel value of a pixel on the preprocessed image less than the critical value, and assigning a second preset value to a pixel value of a pixel on the preprocessed image not less than the critical value;

determining a first spot detection threshold c1 based on the preprocessed image; and identifying a candidate spot on the image based on the preprocessed image and the simplified image, comprising: determining a pixel matrix fulfilling at least two of the following conditions a)-c) as the candidate spot:

a) in the preprocessed image, a center pixel of the pixel matrix has the maximum pixel value, the pixel matrix is represented by r1×r2, both r1 and r2 are odd numbers greater than 1, and the pixel matrix r1×r2 comprises r1×r2 pixels;

b) in the simplified image, the pixel value of the center pixel of the pixel matrix is the second preset value, and the pixel connectivity in the pixel matrix is greater than $$\frac{2}{3} \times r1 \times r2;$$

and c) in the preprocessed image, the pixel value of the center pixel of the pixel matrix is greater than a third preset value, g1×g2 is >c1, g1 is a correlation coefficient of two-dimensional Gaussian distribution in an area of m1×m2 centered on the center pixel of the pixel matrix, g2 is a pixel matrix in the area of m1×m2, both m1 and m2 are odd numbers greater than 1, and the area of m1×m2 comprises m1×m2 pixels.

11. The method according to claim 10, further comprising: determining whether the candidate spot is a spot, comprising:

determining a second spot detection threshold based on the preprocessed image, and determining a candidate spot with a pixel value not less than the second spot detection threshold as a spot.

12. The method according to claim 11, wherein the pixel value of the candidate spot is the pixel value of a pixel to which coordinates of the candidate spot correspond.

13. The method according to claim 11, wherein determining whether the candidate spot is a spot comprises:

dividing the preprocessed image into a set of blocks of a predetermined size;

sorting pixels in the block by pixel value to determine the second spot detection threshold corresponding to the block; and determining a candidate spot in the block with a pixel value not less than the second spot detection threshold corresponding to the block as a spot.

14. The method according to claim 10, wherein preprocessing the image comprises:

determining a background of the image using opening operation;

converting the image into a first image based on the background using top-hat operation;

performing Gaussian blur on the first image to give a second image; and sharpening the second image to give the preprocessed image.

15. The method according to claim 14, wherein determining a critical value to simplify the preprocessed image so as to give a simplified image comprises:

determining the critical value based on the background and the preprocessed image; and comparing pixel values of pixels on the preprocessed image with the critical value so as to give a simplified image.

16. The method according to claim 10, wherein g2 is a corrected pixel matrix in the area of m1×m2, and the correction is performed based on the proportion of pixels with the second preset pixel value in the corresponding area of m1×m2 in the simplified image.

17. The method according to claim 1, further comprising: matching spots on images acquired from a base extension to the spot set corresponding to the sequencing template, and performing base calling according to the matched spots, wherein a plurality of nucleic acid molecules with an optically detectable label are present in the field of view corresponding to the images acquired from the base extension, at least part of the nucleic acid molecules are present as spots in the images acquired from the base extension.

18. The method according to claim 17, wherein, if a distance between any spot in the spot set corresponding to the sequencing template and any spot on the images acquired from the base extension is less than a third predetermined pixel, it is determined that the spot on the images acquired from the base extension matches the spot set corresponding to the sequencing template.

19. A device for constructing a sequencing template based on images, wherein the images comprise a first image, a second image, a third image and a fourth image of the same field of view respectively corresponding to base extensions of four types bases A, T/U, G and C; a plurality of nucleic acid molecules with optically detectable labels are present in the field of view during the base extension, and at least part of the nucleic acid molecules are present as spots on the images; sequential and/or simultaneous completion of the base extensions of the four types of bases is defined as one cycle of sequencing;

the first image comprises an image M1 and an image M2, the second image comprises an image N1 and an image N2, the third image comprises an image P1 and an image P2, and the fourth image comprises an image Q1 and an image Q2;

the images M1 and M2 respectively come from two cycles of sequencing, the images N1 and N2 respectively come from two cycles of sequencing, the images P1 and P2 respectively come from two cycles of sequencing, and the images Q1 and Q2 respectively come from two cycles of sequencing; and the device comprises:

a combining unit, configured for combining any two of the images M1, M2, N1, N2, P1, P2, Q1 and Q2 for spot matching, such that the images M1, M2, N1, N2, P1, P2, Q1 and Q2 each participate in at least one combination to give a plurality of combination images each comprising a first overlap spot, with two or more spots distanced by less than a first predetermined pixel on a combination image being defined as a first overlap spot; and a merging unit, configured for merging the first overlap spots on the plurality of combination images from the combining unit to give a spot set corresponding to the sequencing template.

20. A computer program product comprising an instruction stored in a non-transitory computer readable media, wherein the instruction causes a computer to execute the method according to claim 1 when the program is executed by the computer.

* * * * *